United States Patent [19]

Jefferies et al.

[11] Patent Number: 4,875,858
[45] Date of Patent: Oct. 24, 1989

[54] METHOD AND COMPOSITION FOR DETECTING DENTIN

[75] Inventors: Steven R. Jefferies, Milford; Chin-Teh Huang, Dover, both of Del.

[73] Assignee: Dentsply Research & Development Corp., Milford, Del.

[21] Appl. No.: 222,686

[22] Filed: Jul. 21, 1988

[51] Int. Cl.[4] .............................. A61C 5/00; A61C 5/04
[52] U.S. Cl. ....................................... 433/226; 106/35; 424/7.1; 424/9; 424/49; 433/215; 433/216; 433/217.1; 433/228.1
[58] Field of Search ................. 424/7.1, 9, 49; 106/35; 433/215, 216, 217.1, 226, 228.1

[56] References Cited

U.S. PATENT DOCUMENTS

| | | | |
|---|---|---|---|
| 3,309,274 | 3/1967 | Brilliant | 424/7.1 |
| 3,903,252 | 9/1975 | Stearns et al. | 424/7.1 |
| 3,992,515 | 11/1976 | Johnson | 424/7.1 |
| 4,064,229 | 12/1977 | Block et al. | 424/7.1 |
| 4,198,243 | 4/1980 | Tamaka | 433/24 |
| 4,224,023 | 9/1980 | Cheung | 433/216 |
| 4,302,439 | 11/1981 | Selwyn | 424/7.1 |
| 4,431,628 | 2/1984 | Gaffar | 424/7.1 |
| 4,661,070 | 4/1987 | Friedman | 433/215 |

FOREIGN PATENT DOCUMENTS

| | | |
|---|---|---|
| 944693 | 4/1974 | Canada . |
| 953624 | 8/1974 | Canada . |
| 1087981 | 10/1980 | Canada . |

OTHER PUBLICATIONS

Hosoda et al., *Int. Dent. J.* Mar. 1984, vol. 34, No. 1, pp. 1–12 [Abstract].
Iwaku *Nippon Shika Ishikai Zasshi* 1982, vol. 34, No. 10, p. 1047.
Sato et al., *J. Dent. Res.* Jul.-Aug. 1976, vol. 55, No. 4, p. 678 [Abstract].
*Scandinavian J. Dent. Research* 1985 vol. 93, No. 2, p. 139 [Abstract].
Dederich et al., *J. of Endodontis*, 1985, vol. 11, No. 3, p. 142 [Abstract].
Anderson et al., *J. Dent. Res.* 1984, vol. 63, p. 317 [Abstract].
Leach, C. "Staining Technique for Teaching Preparation Depth in Natural Teeth" *J. Dent. Educ.* vol. 47, No. 9, 1983 pp. 626–628.

Primary Examiner—Paul Lieberman
Assistant Examiner—Linda D. Skaling
Attorney, Agent, or Firm—David E. Wheeler; Edward J. Hanson, Jr.

[57] ABSTRACT

A method of detecting dentin is provided. Also provided is a method of repairing a tooth in which dentin is detected using a substance that stains protein, and is thereby clearly delineated from enamel, the enamel is then selectively acid etched, taking care that none of the acid from the etching procedure contacts dentin, and composite filling material is applied to the tooth. The use of a composition for staining dentin is also provided.

6 Claims, No Drawings

METHOD AND COMPOSITION FOR DETECTING DENTIN

BACKGROUND

The present invention relates to a method and composition for selectivity staining dentin so that the relative positions of dentin and enamel in a tooth preparation can be observed, making possible the independent preparation of enamel and dentin.

As is known to those skilled in the art, composites such as are disclosed in copending Ser. No. 040,636, filed Apr. 21, 1987 (incorporated herein by reference) are increasingly becoming accepted as filling materials, in place of amalgam, in tooth restorations.

A tooth consists of three essential parts, a rather soft center called the pupa which contains the nerves of the tooth, a relatively hard proteinaceous dentin, and a very hard enamel coating. The enamel is relatively non-porous and is resistant to penetration by foreign substances, whereas the dentin is relatively porous because it is living tissue. It is difficult, however, for the practitioner to detect the difference between enamel and dentin using the naked eye.

In the preparation of a composite tooth restoration, it is sometimes desirable to acid etch the tooth enamel in the area adjacent to the cavity or tooth wall requiring restoration so that the composite material can be bonded to the enamel to provide a mechanical retention of the composite. It has been shown in the art that acid etching of the enamel increases the bond strength between composite materials and enamel. Because dentin is living tissue, however, if acid from the acid etching procedure contacts the dentin, the acid may harm the dentin and may cause the patient great pain. Also, placing composite materials over injured dentin tissue may lead to future complications in the tooth.

There are stains known in the art which will stain plaque, which makes it easier for the practitioner to remove plaque. It is known in the art that plaque is bacteria generated protein. It has been discovered in accordance with this invention that known substances used to stain plaque will also stain dentin, providing a line of demarcation between dentin and enamel in a tooth preparation, since enamel is not proteinaceous, and will not be stained by the substances.

Accordingly, it is the object of the invention to make the preparation of composite restoratives easier and safer.

SUMMARY OF THE INVENTION

A method of repairing a tooth using composite filling material is provided. The method comprises preparing a tooth cavity for receiving a composite filling material, and applying a dentin stain to the tooth to reveal the relative location of dentin and enamel in the tooth. When the enamel can be clearly differentiated from the dentin, the enamel is acid etched. After the enamel is acid etched, the stain may be removed from the dentin by using a bleaching agent, and the cavity can then be filled with composite filling material.

Also provided is a method of selectively staining dentin in a structure containing dentin comprising applying a substance that selectively stains dentin to the structure.

Also provided is the use of a composition for staining dentin in which the composition comprises Red D and C 28.

It has been found that using the method of the invention, and the composition described herein, that acid etching of enamel may be obtained substantially without contaminating adjacent dentin with the acid. The method of the invention thereby promotes the health of the tooth and reduces the possibility of tooth pain caused by the presence of acid in the dentin.

DETAILED DESCRIPTION OF THE INVENTION

A method of repairing a tooth using a composite filling material is provided, for example, in the restoration of a carious tooth. According to the method, a tooth is prepared for receiving material in a conventional manner using high speed drills to remove enamel and make an initial cavity in the tooth, and various burs to further clear carious material from the dentin.

When the tooth has been thus prepared, a staining material which stains dentin but does not stain enamel is applied to the tooth. Preferably the staining material (dentin stain) will be applied in the form of a gel so that contact time between the stain and the dentin can be maximized. Any material known in the art which will stain protein may be used as the dentin stain, subject only to the limitation that the stain must be capable of being removed from the dentin when desired prior to the filling of the tooth.

In general, composite materials are generally designed and prepared so that they have light transmitting properties, so that a good aesthetic affect can be obtained using composite filling materials. If composite filling materials are applied over the stain, in some cases this may have a detrimental effect on the aesthetic properties of the restored tooth.

In the method it is preferred to use a staining substance known in the art as Red D and C 28 (the disodium salt of 2,4,5,7-tetrabromo-9-(3,4,5,6-tetrachloro-O-carboxyphenyl-6-hydroxy-3-isoxanthone) as the dentin stain, which stains the exposed dentin of the tooth a red color, while having no effect on the enamel of the tooth.

In those applications where it is not necessary to remove the stains before application of the composite material, the stain may be used as a marker for application of dentin adhesive selectively to the dentin.

After the dentin has been stained excess gel is removed by simply scraping it away, providing a clear line of demarcation between the dentin and the enamel. The enamel can then be acid etched, using procedures known in the art, taking care that none of the acid used in the etching process comes in contact with any of the stained areas of the tooth.

After the acid etching procedure is complete, the stain may, if desirable, be removed from the dentin using conventional prophy procedures, or by rinsing with a solution of sodium hypochlorite or other acceptable bleaching agent.

The composite filling material can then be applied to the tooth as is conventional in the art.

As will be apparent to those skilled in the art, the above general procedure can be used to stain, and thereby detect dentin in substantially any structure containing dentin. This method can be used when it is possible to selectively stain dentin in the structure, leaving other portions of the structure unaffected.

Such a method is made possible using the discovery, as described herein, that certain substances known for staining plaque can also be used to stain dentin.

Such a substance known in the art for staining plaque is Red D and C 28. It has been discovered that this substance, alone, will stain dentin, but it has been found desirable to formulate the substance with a diluent, a gelling agent and a preservative to better facilitate the appliction of the substance to tooth preparation.

Accordingly, in the preferred embodiment the dentin stain composition of the invention comprises Red D and C 28, water, Natrasol 250 HR (hydroxyethylethercellulose, available from Aqualon Company, 1313 North Market Street, Wilmington, DE 19894) and methylparabin.

The composition of the invention preferably has the following approximate composition:

|  | Wt % |
| --- | --- |
| Red D and C 28 | 0.49 |
| Water | 97.26 |
| Natrasol 250 HR | 1.96 |
| methylparabin | 0.29 |
| TOTAL | 100.00 |

The benefits of the composition and method of the invention are illustrated by the bond strengths that are achieved using the method.

| Bond Strengths | | |
| --- | --- | --- |
| Substrate | expt. | X(5.8.)N |
| Dentin | *LCH23-72 | 1,714(601)5 |
| Etched Enamel | *LCH23-72 | 5,349(3409)5 |

*LCH23-72 is Prisma Bond, a product of Dentsply International.

It has been found that the short term application of the dentin staining composition to freshly cut dentin and enamel does not impair the subsequent ability of the cut surfaces to be bonded by dentin adhesives (such as Prisma Universal Bond) or enamel to be bonded by the acid-etch process.

While present embodiments of the invention and methods of practicing the same have been illustrated and described, it will be recognized by those skilled in the art that the invention may be otherwise variously embodied and practiced within the scope of the following claims.

What is claimed is:

1. A method of repairing a tooth using a composite filling material, comprising the steps of:
    (a) preparing a tooth cavity for receiving a composite filling material;
    (b) applying a dentin stain to said tooth revealing the relative locations of dentin and enamel wherein said dentin stain stains said dentin while not affecting said enamel;
    (c) etching the enamel while avoiding contacting the stained dentin with etching composition;
    (d) removing the stain from the dentin using a bleaching agent; and
    (e) filling the cavity with composite filling material.

2. The method of claim 1 comprising the steps of applying a dentin stain comprising a gel consisting essentially of the disodium salt of 2,4,5,7-tetrabromo-9-(3,4,5,6-tetrachloro-O-carboxyphenyl-6-hydroxy-3-isoxanthone), water, hydroxyethyl-ether cellulose and methylparabin.

3. The method of claim 1 comprising the step of etching the enamel using an acid etch.

4. The method of claim 1 comprising the step of removing the stain from dentin using sodium hypochlorite.

5. A method of repairing a tooth comprising the steps of
    (a) preparing a tooth cavity for receiving a dental filling material;
    (b) applying a dentin stain to said tooth revealing the relative locations of dentin and enamel wherein said dentin stain stains said dentin while not affecting said enamel;
    (c) etching the enamel while avoiding contacting the stained dentin with etching composition; and
    (d) filling the cavity with dental filling material.

6. The method of claim 5 which further comprises the steps of
    (a) removing stain from dentin using a bleaching agent immediately after the enamel is etched; and
    (b) filling the cavity with a dental filling material which is a composite filling material.

* * * * *